US008131049B2

(12) United States Patent
Ruth et al.

(10) Patent No.: US 8,131,049 B2
(45) Date of Patent: *Mar. 6, 2012

(54) BREAST TOMOSYNTHESIS WITH DISPLAY OF HIGHLIGHTED SUSPECTED CALCIFICATIONS

(75) Inventors: Chris Ruth, Boxford, MA (US); Jay Stein, Boston, MA (US); Loren Niklason, Hillsborough, NC (US); Andrew Smith, Lexington, MA (US)

(73) Assignee: Hologic, Inc., Bedford, MA (US)

( * ) Notice: Subject to any disclaimer, the term of this patent is extended or adjusted under 35 U.S.C. 154(b) by 142 days.

This patent is subject to a terminal disclaimer.

(21) Appl. No.: 12/605,031

(22) Filed: Oct. 23, 2009

(65) Prior Publication Data
US 2010/0086188 A1    Apr. 8, 2010

Related U.S. Application Data

(63) Continuation of application No. 11/903,021, filed on Sep. 20, 2007, now Pat. No. 7,630,533.

(51) Int. Cl.
*G06K 9/00* (2006.01)
(52) U.S. Cl. ......... 382/131; 382/132; 382/284; 382/286
(58) Field of Classification Search .................. 382/131, 382/132, 154, 284, 286, 291
See application file for complete search history.

(56) References Cited

U.S. PATENT DOCUMENTS

| | | | |
|---|---|---|---|
| 3,502,878 A | 3/1970 | Stewart | |
| 3,863,073 A | 1/1975 | Wagner | |
| 3,971,950 A | 7/1976 | Evans et al. | |
| 4,160,906 A | 7/1979 | Daniels et al. | |
| 4,310,766 A | 1/1982 | Finkenzeller et al. | |
| 4,496,557 A | 1/1985 | Malen et al. | |
| 4,559,641 A | 12/1985 | Caugant et al. | |
| 4,706,269 A | 11/1987 | Reina et al. | |
| 4,744,099 A | 5/1988 | Huettenrauch et al. | |
| 4,773,086 A | 9/1988 | Fujita et al. | |
| 4,773,087 A | 9/1988 | Plewes | |
| 4,819,258 A | 4/1989 | Kleinman et al. | |
| 4,821,727 A | 4/1989 | Levene et al. | |
| 4,969,174 A | 11/1990 | Scheid et al. | |
| 4,989,227 A | 1/1991 | Tirelli et al. | |
| 5,018,176 A | 5/1991 | Romeas et al. | |
| RE33,634 E | 7/1991 | Yanaki | |

(Continued)

FOREIGN PATENT DOCUMENTS
EP          0775467 A1    5/1997
(Continued)

OTHER PUBLICATIONS

Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.

(Continued)

*Primary Examiner* — Phuoc Tran
(74) *Attorney, Agent, or Firm* — Cooper & Dunham, LLP

(57) ABSTRACT

Systems and methods that facilitate the presentation and assessment of selected features in projection and/or reconstructed breast images, such as calcifications that meet selected criteria of size, shape, presence in selected slice images, distribution of pixels that could be indicative of calcification relative to other pixels or of other image features of clinical interest.

47 Claims, 5 Drawing Sheets

U.S. PATENT DOCUMENTS

| | | |
|---|---|---|
| 5,029,193 A | 7/1991 | Saffer |
| 5,051,904 A | 9/1991 | Griffith |
| 5,078,142 A | 1/1992 | Siczek et al. |
| 5,163,075 A | 11/1992 | Lubinsky et al. |
| 5,164,976 A | 11/1992 | Scheid et al. |
| 5,199,056 A | 3/1993 | Darrah |
| 5,240,011 A | 8/1993 | Assa |
| 5,289,520 A | 2/1994 | Pellegrino et al. |
| 5,359,637 A | 10/1994 | Webber |
| 5,365,562 A | 11/1994 | Toker |
| 5,415,169 A | 5/1995 | Siczek et al. |
| 5,426,685 A | 6/1995 | Pellegrino et al. |
| 5,452,367 A | 9/1995 | Bick et al. |
| 5,506,877 A | 4/1996 | Niklason et al. |
| 5,526,394 A | 6/1996 | Siczek et al. |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzke et al. |
| 5,609,152 A | 3/1997 | Pellegrino et al. |
| 5,627,869 A | 5/1997 | Andrew et al. |
| 5,657,362 A | 8/1997 | Giger et al. |
| 5,668,889 A | 9/1997 | Hara |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,872,828 A | 2/1999 | Niklason et al. |
| 5,878,104 A | 3/1999 | Ploetz |
| 5,896,437 A | 4/1999 | Ploetz |
| 5,970,164 A | 10/1999 | Bamberger et al. |
| 5,986,662 A | 11/1999 | Argiro et al. |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers et al. |
| 6,137,527 A | 10/2000 | Abdel-Malek et al. |
| 6,141,398 A | 10/2000 | He et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,256,370 B1 | 7/2001 | Yavuz |
| 6,272,207 B1 | 8/2001 | Tang |
| 6,289,235 B1 | 9/2001 | Webber et al. |
| 6,292,530 B1 | 9/2001 | Yavus et al. |
| 6,327,336 B1 | 12/2001 | Gingold et al. |
| 6,341,156 B1 | 1/2002 | Baetz et al. |
| 6,375,352 B1 | 4/2002 | Hewes et al. |
| 6,411,836 B1 | 6/2002 | Patel et al. |
| 6,415,015 B2 | 7/2002 | Nicolas et al. |
| 6,442,288 B1 | 8/2002 | Haerer et al. |
| 6,459,925 B1 | 10/2002 | Nields et al. |
| 6,501,819 B2 | 12/2002 | Unger et al. |
| 6,556,655 B1 | 4/2003 | Chichereau et al. |
| 6,597,762 B1 | 7/2003 | Ferrant et al. |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,630,937 B2 | 10/2003 | Kallergi et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,744,848 B2 | 6/2004 | Stanton et al. |
| 6,748,044 B2 | 6/2004 | Sabol et al. |
| 6,751,285 B2 | 6/2004 | Eberhard et al. |
| 6,758,824 B1 | 7/2004 | Miller et al. |
| 6,813,334 B2 | 11/2004 | Koppe et al. |
| 6,882,700 B2 | 4/2005 | Wang et al. |
| 6,885,724 B2 | 4/2005 | Li et al. |
| 6,912,319 B1 | 6/2005 | Barnes et al. |
| 6,940,943 B2 | 9/2005 | Claus et al. |
| 6,978,040 B2 | 12/2005 | Berestov |
| 6,999,554 B2 | 2/2006 | Mertelmeier |
| 7,110,490 B2 | 9/2006 | Eberhard et al. |
| 7,110,502 B2 | 9/2006 | Tsuji |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,149,335 B2 | 12/2006 | Kaufhold |
| 7,245,694 B2 | 7/2007 | Jing et al. |
| 7,295,691 B2 | 11/2007 | Uppaluri et al. |
| 7,315,607 B2 | 1/2008 | Ramsauer |
| 7,319,735 B2 | 1/2008 | Defreitas et al. |
| 7,323,692 B2 | 1/2008 | Rowlands et al. |
| 7,352,885 B2 | 4/2008 | Eberhard et al. |
| 7,430,272 B2 | 9/2008 | Jing et al. |
| 7,443,949 B2 | 10/2008 | Defreitas et al. |
| 7,577,282 B2 * | 8/2009 | Gkanatsios et al. ......... 382/128 |
| 7,630,533 B2 * | 12/2009 | Ruth et al. ................ 382/131 |
| 2001/0038681 A1 | 11/2001 | Stanton et al. |
| 2002/0012450 A1 | 1/2002 | Tsujii |
| 2002/0050986 A1 | 5/2002 | Inouc et al. |
| 2002/0075997 A1 | 6/2002 | Unger et al. |
| 2002/0097902 A1 | 7/2002 | Roehrig et al. |
| 2003/0018272 A1 | 1/2003 | Treado et al. |
| 2003/0073895 A1 | 4/2003 | Nields et al. |
| 2003/0095624 A1 | 5/2003 | Eberhard et al. |
| 2003/0194050 A1 | 10/2003 | Eberhard et al. |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0215120 A1 | 11/2003 | Uppaluri et al. |
| 2004/0066884 A1 | 4/2004 | Hermann Claus et al. |
| 2004/0094167 A1 | 5/2004 | Brady et al. |
| 2004/0100476 A1 | 5/2004 | Morita et al. |
| 2004/0101095 A1 | 5/2004 | Jing et al. |
| 2004/0109529 A1 | 6/2004 | Eberhard et al. |
| 2004/0171986 A1 | 9/2004 | Tremaglio, Jr. et al. |
| 2004/0267157 A1 | 12/2004 | Miller et al. |
| 2005/0002550 A1 | 1/2005 | Jabri et al. |
| 2005/0049521 A1 | 3/2005 | Miller et al. |
| 2005/0063509 A1 | 3/2005 | DeFreitas et al. |
| 2005/0078797 A1 | 4/2005 | Danielsson et al. |
| 2005/0089205 A1 | 4/2005 | Kapur et al. |
| 2005/0105679 A1 | 5/2005 | Wu et al. |
| 2005/0113681 A1 | 5/2005 | DeFreitas et al. |
| 2005/0113715 A1 | 5/2005 | Schwindt et al. |
| 2005/0113961 A1 | 5/2005 | Sabol et al. |
| 2005/0129172 A1 | 6/2005 | Mertelmeier |
| 2005/0135555 A1 | 6/2005 | Claus et al. |
| 2005/0135664 A1 | 6/2005 | Kaufhold et al. |
| 2005/0226375 A1 | 10/2005 | Eberhard et al. |
| 2006/0030784 A1 | 2/2006 | Miller et al. |
| 2006/0067473 A1 | 3/2006 | Eberhard et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0155209 A1 | 7/2006 | Miller et al. |
| 2006/0210131 A1 | 9/2006 | Wheeler, Jr. et al. |
| 2006/0269114 A1 | 11/2006 | Metz |
| 2006/0291618 A1 | 12/2006 | Eberhard et al. |
| 2007/0003117 A1 | 1/2007 | Wheeler et al. |
| 2007/0003118 A1 | 1/2007 | Wheeler et al. |
| 2007/0014448 A1 | 1/2007 | Wheeler et al. |
| 2007/0030949 A1 | 2/2007 | Jing et al. |
| 2007/0036265 A1 | 2/2007 | Jing et al. |
| 2007/0052700 A1 | 3/2007 | Wheeler et al. |
| 2007/0076844 A1 | 4/2007 | Defreitas et al. |
| 2007/0076928 A1 | 4/2007 | Claus et al. |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0045833 A1 | 2/2008 | Defreitas et al. |
| 2008/0130979 A1 | 6/2008 | Ren et al. |
| 2009/0003519 A1 | 1/2009 | Defreitas et al. |
| 2009/0010384 A1 | 1/2009 | Jing et al. |
| 2009/0080594 A1 | 3/2009 | Brooks et al. |
| 2009/0080602 A1 | 3/2009 | Brooks et al. |

| | | | |
|---|---|---|---|
| 2009/0135997 | A1 | 5/2009 | Defreitas et al. |
| 2009/0268865 | A1 | 10/2009 | Ren et al. |
| 2009/0296882 | A1 | 12/2009 | Gkanatsios et al. |
| 2009/0304147 | A1 | 12/2009 | Jing et al. |
| 2010/0054400 | A1 | 3/2010 | Ren et al. |
| 2010/0086188 | A1 | 4/2010 | Ruth et al. |
| 2010/0195882 | A1 | 8/2010 | Ren et al. |
| 2010/0226475 | A1 | 9/2010 | Smith et al. |

FOREIGN PATENT DOCUMENTS

| | | |
|---|---|---|
| EP | 0982001 A1 | 3/2000 |
| EP | 1428473 A2 | 6/2004 |
| WO | WO 90/05485 | 5/1990 |
| WO | WO 98/16903 | 4/1998 |
| WO | WO 00/51484 | 9/2000 |
| WO | WO 03/020114 A2 | 3/2003 |
| WO | WO 2005/051197 A1 | 6/2005 |
| WO | WO 2005110230 A1 | 11/2005 |
| WO | WO 2005112767 A1 | 12/2005 |
| WO | WO 2006/055830 A2 | 5/2006 |
| WO | WO 2006/058160 A2 | 6/2006 |

OTHER PUBLICATIONS

Digital Clinical Reports, Tomosynthesis, GE Brochure 98-5493, Nov. 1998.

Mammographic Accreditation Phantom, http://www.cirsinc.com/pdfs/015cp.pdf.

Heang-Ping Chan et al., "ROC study of the effect of stereoscopic imaging on assessment of breast lesions", Medical Physics, vol. 32, No. 4, Apr. 2005.

Cole, Elodia, et al., "The Effects of Gray Scale Image Processing on Digital Mammography Interpretation Performance", *Academic Radiology*, vol. 12, No. 5, pp. 585-595, May 2005.

Federica Pediconi et al., "Color-coded automated signal intensity-curve for detection and characterization of breast lesions: Preliminary evaluation of a new software for MR-based breast imaging", International Congress Series 1281 (2005) 1081-1086.

"Essentials for life: Senographe Essential Full-Field Digital Mammography system", GE Health-care Brochure, MM-0132-05.06-EN-US, 2006.

Senographe 700 & 800T (GE); 2-page download on Jun. 22, 2006 from.www.gehealthcare.com/inen/rad/whe/products/mswh800t.html.; Figures 1-7 on 4 sheets re lateral shift compression paddle.

"Lorad Selenia" Document B-BI-SEO US/Intl (May 2006) copy right Hologic 2006.

"Filtered Back Projection," (NYGREN) published May 8, 2007; URL: http://web.archive.org/web/19991010131715/http://www.owlnet.rice.edu/ -elec539/Projects97lt/node2.html.

Smith, A., "Fundamentals of Breast Tomosynthesis", White Paper, Hologic Inc., WP-00007, Jun. 2008.

* cited by examiner

BREAST TOMOSYNTHESIS WITH DISPLAY OF HIGHLIGHTED SUSPECTED CALCIFICATIONS

REFERENCE TO RELATED APPLICATIONS

This application is a Rule 1.53(b) continuation of U.S. application Ser. No. 11/903,021, filed Sep. 20, 2007, now U.S. Pat. No. 7,630,533, which is related to earlier-filed applications Ser. Nos. 11/604,069, 11/271,050, 11/059,282, 10/723,486, and 10/305,480 filed, respectively, on Nov. 24, 2006, Nov. 10, 2005, Feb. 16, 2005, Nov. 26, 2003, and Nov. 27, 2002, and is related to PCT applications PCT/US2005/41941 and PCT/US2005/42613 filed, respectively, on Nov. 15 and 23, 2005. This patent specification hereby incorporates by reference the contents of each of the earlier-filed patent applications.

FIELD

This patent specification pertains to x-ray tomosynthesis, and more specifically to techniques and equipment for acquiring, processing, storing and displaying tomosynthesis images, including tomosynthesis projection images and tomosynthesis reconstructed images. An important aspect of this patent specification pertains to identifying and highlighting suspected calcifications in displays of tomosynthesis images.

BACKGROUND AND SUMMARY OF THE DISCLOSURE

X-ray mammography remains a well-established technology, and x-ray tomosynthesis of the breast has been developed recently as discussed in the earlier-filed patent applications identified above. Clinical testing of tomosynthesis systems has been carried out, and the assignee of this patent specification, Hologic, Inc., has demonstrated at trade shows in this country a fused, multimode mammography/tomosynthesis system that takes either or both types of images, either in single or multiple compressions/immobilizations of the breast. Dedicated breast tomosynthesis systems also have been proposed.

Tomosynthesis as used in the systems and methods disclosed in this patent specification typically involves acquiring a plurality of tomosynthesis projection images Tp at respective angles relative to the breast, and using information describing at least these images Tp (or some of the Tp images) to reconstruct a plurality of tomosynthesis reconstructed images Tr representative of respective breast slices that have selective thicknesses and orientations and correspond to respective sections through or slices of the breast that typically are but need not be planar. For example, the slices can be curved in 3D space. In addition, conventional x-ray mammography images Mp can be acquired, in the same procedure that acquires the Tp images of a breast or in a different procedure and in the same or different compressions of the breast, and may be used in addition to the Tp images or in place of some of the Tp images, in reconstructing Tr images.

Mp images can be processed by various techniques that draw attention to selected portions or features of these images, such as CAD (computer aided detection) techniques that analyze the images to identify likely abnormalities and place markers on a breast image or representation that identify the location and in some cases the type or other information about the likely abnormalities. Some of the parent applications identified above describe applying CAD analysis to Tr and/or Tp images as well, or as an alternative or an adjunct to applying CAD to Mp images, and also describe how to improve the presentations of Tp and/or Tr images (collectively referred to here as T images), Mp images, and CAD and/or other information about the images to make the review by health professionals more effective and efficient.

CAD application to Mp images also is a well-established technology. See, for example, the mammography CAD products offered by R2 Technology, Inc. of Sunnyvale, Calif. and Patent Publications US 2002/0097902 and US 2004/0100476 and U.S. Pat. Nos. 5,970,164, and 6,630,937. In addition to the disclosure of applying CAD to Tp and Tr images in the related applications identified above, U.S. Pat. No. 6,748,044 discusses applying CAD to tomosynthesis images and U.S. Pat. No. 7,149,335 discusses detecting microcalcifications in tomosynthesis images and subtracting background to enhance visibility of the detected microcalcifications. Also possibly relevant to state-of-the-art may be US20030194121A1, U.S. Pat. No. 6,748,044, US20030215120A1, US20050002550A1, US20060269114A1, US20050089205A1, US20050113961A1, U.S. Pat. No. 7,142,633, US20060067473A1, US20060210131A1, US20070003117A1, US20070003118A1, US20070014448A1, US20070052700A1, US20070076928A1. The patents and publication identified in this paragraph also are incorporated by reference in this patent specification.

As more information about the breast becomes available from imaging, an important challenge is to present such information to the health professional effectively and efficiently such that screening for abnormalities can be done thoroughly and effectively, and yet in a reasonable time to be practical, and diagnostic assessment can also be facilitated. For a film mammographic study there usually are four films of the patient's breasts (at least for studies done in the U.S.A.), two CC views and 2 MLO views, that typically can be examined within a few minutes. However, with digital images and particularly tomosynthesis images Tp and Tr, there can be dozens of images and each can be viewed within different windows of pixel values centered at different levels of pixel values. Unless suitable display techniques are developed, information that is in the images may not be fully appreciated or utilized and/or the examination time may become so long as to be impractical, particularly for screening asymptomatic patients but also possibly for diagnostic or other purposes. This patent specification is directed to providing tomosynthesis and like images in a manner that would facilitate extracting useful information from them in a reasonable time.

In this patent specification, the notation Mp refers to a conventional mammogram, which is a two-dimensional x-ray projection image of a breast; the term Mp encompasses both a digital image as acquired by a flat panel detector or another imaging device and the image after conventional processing to prepare it for display to a health professional or for further processing or for storage, e.g. in the PACS system of a hospital or another institution. Mp also encompasses digitized film/screen mammograms. Tp refers to an image that is similarly two-dimensional but is taken at a respective tomosynthesis angle between the breast and the origin of the imaging X-rays (typically the focal spot of an X-ray tube), and also encompasses the image as acquired as well as the image after being processed for display or for some other use. Tr refers to an image that is reconstructed from images Tp, for example in the manner described in said earlier-filed patent applications, and represents a slice of the breast essentially as it would appear in a projection X-ray image of that slice at any desired angle, not only at an angle used for Tp or Mp images. In addition, a Tr image can represent a slice that conforms to any desired surface such as a flat or curved plane. Moreover, the process of reconstructing Tr images can use Mp images in addition to using Tp images or instead of one or more Tp images. The terms Tp, Tr and Mp also encompasses information, in whatever form, that is sufficient to describe such an image for display, further processing, or storage. The images Mp, Tp and Tr typically are in digital form before being displayed, and can be defined by information identifying properties of each pixel in a two-dimensional array of pixels, although other ways to describe the images can be used as well or instead. The pixel values typically relate to respective measured or estimated or computed responses to X-rays of corresponding volumes in the breast (voxels or columns of tissue). A Tr image can represents a thin slice of a breast, in which case it may consist of pixel values representing respective voxels (volume elements) of the breast that are in a single layer or a few layers transverse to the direction of the x-ray beam, or a Tr image may represent a thicker slice of the breast, in which case the pixel values of the thick-slice Tr image can represent columns of tissue along the direction of the x-ray beam and are calculated using known techniques such as, without limitation, a normalized projection of the pixels of several contiguous thin-slice images onto an image plane, a MW (maximum intensity projection), or some other way of combining the pixel values representing several thin-slice images. As a non-limiting example, a thin-slice Tr image can represent a 1 mm thick slice of the imaged breast and a thick-slice Tr image can represent a 5-20 mm thick slice of the breast. Thus, when a breast is compressed for x-ray imaging to a thickness of 5-6 cm, there can be 50-60 thin-slice Tr images and 3-12 thick-slice Tr images.

Microcalcifications seen in breast images are considered important clues in screening and/or diagnosis, and prior proposals have been directed to identifying particular specific patterns of microcalcifications or all microcalcifications, or at least those having specified characteristics such as size or density. This patent specification takes a different approach by not only necessarily seeking to identify and classify patterns of microcalcification distributions in images, or to identify or enhance all microcalcifications detectable in the image, but rather to facilitate the visualization of up to a certain number of selected suspected calcifications that meet various special thresholds in a given image or volume of tissue in ways that are particularly useful to the health professional. Calcifications often have a typical x-ray absorption characteristic, but not all objects with these absorption characteristics are calcifications or are of clinical value. Calcifications of clinical interest generally fall in a certain range of sizes and shapes and patterns. The largest calcifications are often benign. Linear ones also are often benign. Identifying all of the very smallest calcification-like objects runs the risk that some of them might represent noise and not true calcifications or reasonably suspected calcifications. One object of the approach disclosed in this patent specification is to reduce the number of identified possible or suspected calcifications which are of lower clinical value.

As one non-limiting example, the approach disclosed in this patent specification involves examining through computer processing the individual Tr images in a 3D set of such images to identify an initial set of possible calcifications that meets a threshold limiting the number of identified calcifications in a given Tr image, or in the entire 3D set or a selected subset of the entire 3D set, to a specified number of calcifications and/or number of pixels that are determined to correspond to calcifications. Preferably, the Tr images are presented for this examination after filtering with a mask that enhances high spatial frequency image features. The process removes from the initial set, pixels initially determined to relate to calcifications that are too large in area or too long in linear extent, and may additionally impose other constraints such as excluding initially determined calcifications that are not present in two adjacent Tr images, applying ligament removal and edge removal techniques, requiring at least a certain number of calcifications to be in a specified volume of the 3D set, and excluding calcifications that are in the initial and trailing Tr images in a stack of Tr images and thus are likely to be at the skin level and unlikely to have clinical significance. The removal processes are designed to remove calcifications that are likely to be devoid of clinical interest and to remove noise and other non-calcification objects. In displaying the results, one example is to show a scout view that generally conforms in shape to a projection of the breast and shows a distribution of identified calcifications as well as a current level that both (1) includes calcifications and (2) corresponds to a Tr image that is orthogonal to the scout image and is seen at a main image display. Alternatively, this information can be displayed using a ruler or other schematic display that does not conform in shape to a projection of the breast but still allows display of the current level and/or the locations of likely calcifications. Thus, the current level in the 2D scout or schematic view points to one or more corresponding Tr images. The scout or schematic view also shows a pointer to a next level that contains identified calcifications so that a user can conveniently click on that level and thus call on the main display the next Tr image of interest. The scout or schematic view may also indicate how many calcification clusters are in a given Tr image. In addition, the user can toggle the main display between showing a Tr image with or without highlighted calcifications therein. A health professional thus can quickly and effectively review Tr images that are likely to be of interest. The health professional can additionally select for the main display additional Tr images, Tr images that are for thick or thin slices and/or reconstructed in another orientation, Tp images and/or Mp images.

An alternative or additional process is to initially search Tp and/or Mp images rather than the 3D set of Tr images to identify likely calcifications of interest. This can be done using CAD as disclosed in the patent literature incorporated by reference in this patent specification, or by adapting the principles discussed above for identifying calcifications in Tr images and 3D volumes, or in some other manner. After likely calcifications of clinical significance are identified in the 2D Tp and/or Mp images, the 2D images can be displayed one at a time or several at a time, or only those 2D images that have identified calcifications can be displayed. When a user points to a likely calcification in a displayed 2D image, e.g., by a mouse click on the calcification in a 2D image, computer processing can search through the Tr images of the breast to identify and display the Tr image or Tr images that contain that calcification. This search through the Tr images can use knowledge about the location of the likely calcification in the 2D image, on parameters of the calcification such as its size, shape, pixel values and distribution of those values in the 2D image, and possibly other parameters. In case of an ambiguity, i.e., the calcification pointed to in the 2D image appears in two or more Tr images, all possibly relevant Tr images can be displayed to the user, singly or in a set or subsets or in cine mode, and the user may select for further use the ones that appear relevant or dismiss any that are not. This alternative can reduce processing time because the search for likely calcifications in the 2D images can be faster, and the subsequent search for the Tr slice(s) that contain a calcification to which the user pointed in a 2D image also can be faster. One reason for greater computational efficiency is that the 3D data set (the Tr images) need to be processed only after a likely calcification has been selected, so only a relatively small volume of the 3D set would need to be searched. Another advantage of this alternative may be if the search process is more sensitive and/or more accurate for 2D images. If so, then it is more likely to decrease the overall rate of false negatives and/or false positives in identifying likely calcifications, and thus improve the presentation of images to the health professional and make the overall process of assessing the images for screening, diagnosis, or other purposes, more effective and/or more efficient.

As another alternative or additional process, the user can point to any feature in one of the 2D images, not necessarily a likely calcification, even in 2D images that have not been processed to identify likely calcifications, and the process can attempt to identify and display for the user the Tr slice(s) in which that feature can be seen well, e.g., the feature is in best focus. The search through the 3D set of pixel data can use information about the feature to which the user pointed, such as location in the 2D image, size, shape, pixel values and distribution of those values, and possibly other parameters. If the feature is relatively unique and small, the process may correctly identify and display for the user one or only a few Tr slices. In other cases, such as in the case of a relatively large mass, or in the case of a feature in the 2D image that represents a superposition of two or more features in the breast that are along the x-ray beam path to that feature in the 2D image, there may be ambiguities as to which Tr image or images show the feature to which the user has pointed. Again, in such a case the process may similarly display the possibly pertinent Tr slices, or may display only those that meet a threshold of relevance, e.g., based on a calculation of their degree of relevance to the feature to which the user pointed.

The discussion above refers to highlighting calcifications. Other methods of emphasizing calcifications also are possible, and are in the scope of this patent specification. These include pointers such as arrows, circling or drawing lines, and the use of changing the color of the display of the calcification, or other methods of presenting visual cues to the viewer to look at specified areas on the image.+

DETAILED DESCRIPTION

Figure 1:
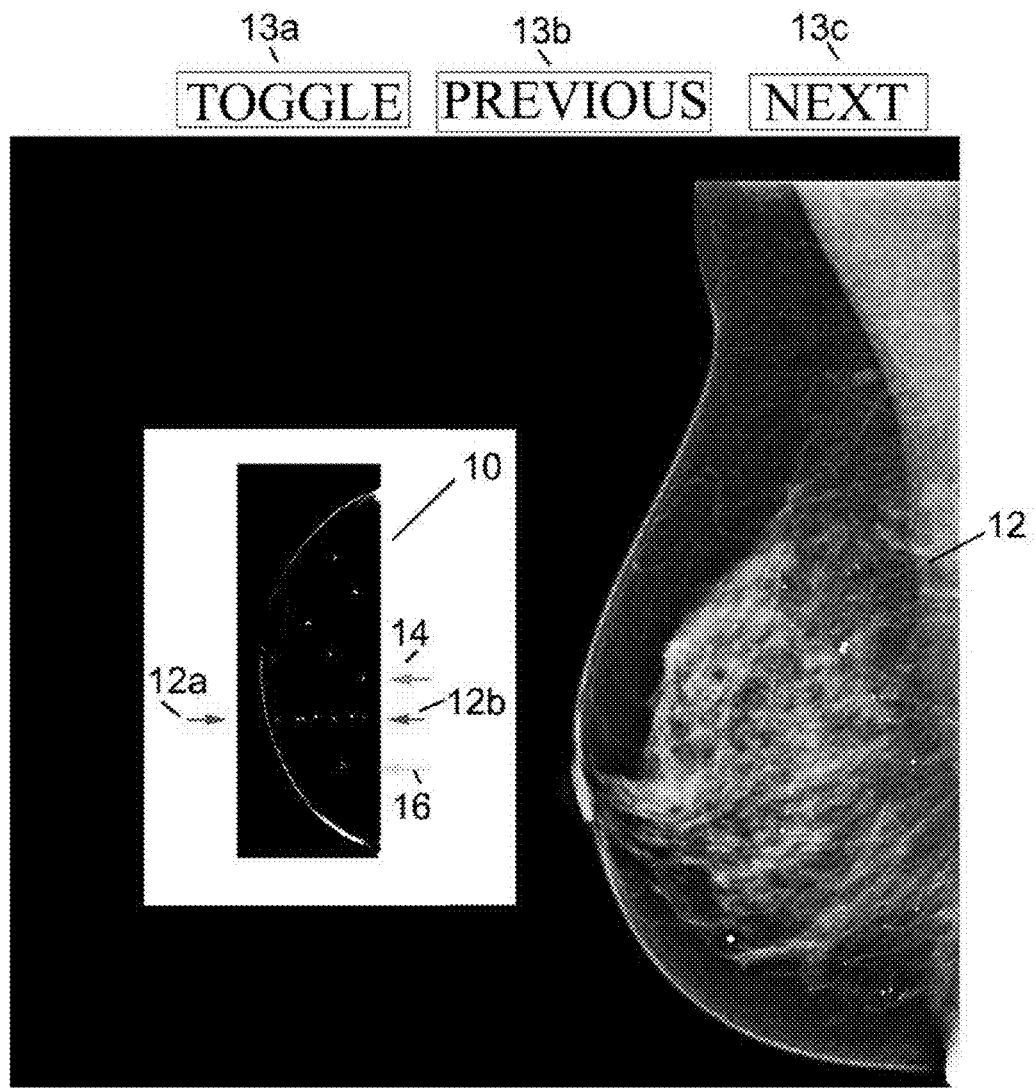
FIG. 1 illustrates an example of a display of a scout image and a reconstructed tomosynthesis slice image Tr.

Referring to FIG. 1, the image on the left is a scout view 10 that generally conforms to an outline of a patient's breast and contains bright dots indicative of calcifications identified through a process described below. Two facing arrows 12a and 12b at the side of scout image 10 point to a level in the scout image that corresponds to a reconstructed tomosynthesis slice image Tr 12 seen at the right side of FIG. 1. The views of images 10 and 12 are mutually orthogonal. Tr image 12 in this example has highlighted calcifications (seen as white dots) that are more numerous than those seen in scout image 10, for reasons that will become apparent from the disclosure below. Next to scout image 10 are an arrow 14 that points to the next level up in image 10 that contains calcifications and an arrow 16 that points to the next level below in image 10 that contains calcifications. By clicking on arrow 14 or arrow 16 the user can call for display at 12 the corresponding Tr image. Tr image 12 can be displayed without highlighting its suspected calcifications, as a normal Tr image, by a user command such as clicking a mouse button or through some other interface. The Tr image that is displayed as image 12 can be for a thin slice, e.g., a 1 mm or somewhat thinner or thicker slice of breast tissue, or for a thick slice such as a 3 mm or somewhat thinner or thicker slice of breast tissue, in which case the thick-slice image can be formed by combining several thin slice Tr image through a known process such as, without limitation, adding with or without normalization, MIP projection, etc. Alternatively, data representing Tp images can be reconstructed into data representing thick-slice Tr images in the reconstruction process using known techniques such as using appropriate backprojection or frequency domain filters. The user can click on button 13a, 13b and 13c to toggle display 12 between a Tr image with and without highlighted suspected calcification, or to the previous and next Tr images.

Figure 4:
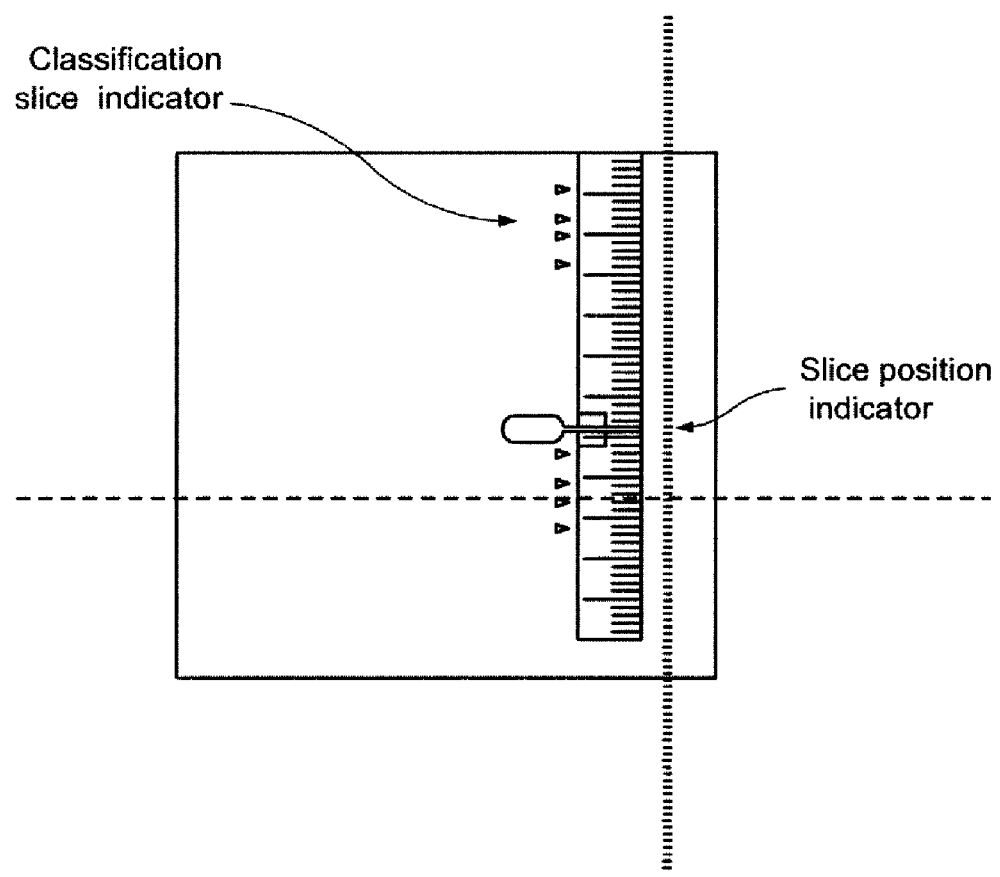
FIG. 4 illustrates a method of displaying a current slice and locations of calcifications.

FIG. 4 shows an alternative method to the scout view for identifying slice locations for calcifications. This involves a ruler that indicates both the currently-displayed slice, in terms of its height or position in a stack of Tr images and corresponding slices of breast tissue (using a marker such as the one labeled "Slice position indicator" in FIG. 4), and also Calcification slice indicator marks that show the slices where potential calcifications have been identified (by marks such as the arrows labeled "Calcification slice indicator" in FIG. 4).

Figure 5:
FIG. 5 illustrates a method of identifying calcifications on a tomosynthesis slice image Tr.

FIG. 5 shows an alternative method for identifying calcifications that does not require highlighting them. In this figure, potential calcifications are outlined by a box such as the one labeled "Square indicating calcifications" in FIG. 5. Arrows pointing to the calcifications would be an alternative method, as would other marks and or lines and or color and/or intensity changes on the image in the vicinity of the calcifications.

Figure 2:
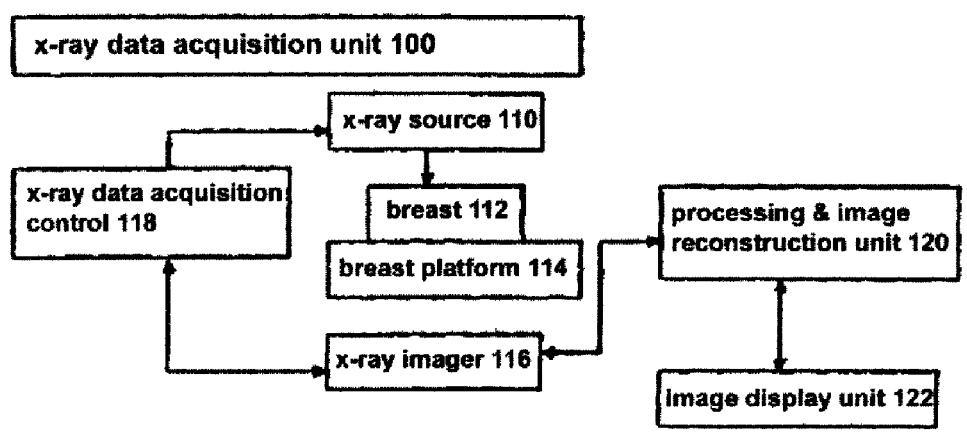
FIG. 2 illustrates in block diagram form a mammography/tomosynthesis system that can be used to acquire breast imaging x-ray data and process and display the data according to preferred embodiments of the approach disclosed in this patent specification.

X-ray data for use in the process disclosed in this patent specification can be acquired, processed, and displayed by the system illustrated in FIG. 2 as a high level integration of sub-systems discussed in greater detail in the documents incorporated by reference in this patent specification. In FIG. 2, an x-ray data acquisition unit 100 includes an x-ray source 110 imaging a patient's breast 112 supported on a breast platform 114. An x-ray imager 116 such as a flat panel, direct conversion imager available from Hologic, Inc. of Bedford, Mass., generates projection image data such as data defining images Mp and/or Tp. X-ray source 110 is mounted for movement around breast platform 114 so that images Tp (and Mp, if desired) can be taken at a number of different angles for a specific orientation of breast platform 114, such as a generally CC orientation or a generally MLO orientation. X-ray imager 116 can be stationary but preferably it also moves relative to breast platform 114, in a specified synchronous relationship to source 110, preferably in a manner that keeps the imaging plane at the same angle to the imaging x-ray beam. Units 110 and 116 communicate with x-ray data acquisition control 118 that controls the operation of the system as known from said material incorporated by reference. X-ray data from imager 116 is delivered to processing and image reconstruction unit 120 that includes one or more programmed digital computers, where data is processed as known into Tp and possibly Mp images and into Tr images and where the process described below is carried out. The resulting information is displayed at image display unit 122. The software for any specific implementation of specific data processing hardware can be written without undue experimentation by a person skilled in the art based on the disclosure of this patent specification. The details of such implementation would depend to a certain extent on factors such as the hardware and operating systems that a particular designer or user would select, and many variations are possible. For the sake of both clarity and conciseness such details that are within the skill of the art once the disclosure herein is available, are not included in this patent specification.

The processing carried out by unit 120 typically includes known filtering and preliminary processing of the Tp image data (and any Mp data used in addition to or instead of Tp image data) and reconstruction of thin and/or thick slice Tr image data that defines a 3D set of pixel values. The 3D set is made up of the pixel values representing an x-ray property of respective pixels of each of a number of Tr images, each Tr image representing a respective slice of breast tissue. Preferably, the Tr images used in steps 1-4 below represent thin slices of the breast, such as 1 mm slices, but using thicker slice images is not excluded. These pixel values are processed in the following principal steps as a non-limiting preferred example following a filtering of the Tr images individually to suppress low spatial frequency components. Any one of a number of known filtering processes can be used, such as a process involving the use of unsharp mask filters.

1. Compute and use a threshold to form a first provisional set of pixels that are candidates for inclusion in a final set of pixels that are determined to be associated with calcifications and called "calc pixels" below. The objective is to include in the final set of calc pixels no more than a selected number N of pixels for the entire 3D set of pixels defining the Tr images. For example, candidate calc pixels can be identified in this step by provisionally identifying as calc pixels the pixels that have pixel values exceeding a provisional threshold level. This can be done by processing only the pixel values in one or several Tr images that may correspond to centrally located breast tissue, or it can be done for the entire 3D set. As a non-limiting example, if pixel values in a particular system are adjusted to range from −60 to +60 units in value in a Tr image after filtering per step 1 above, any pixel that has a value greater than, e.g., 40 can be provisionally classified as a calc pixel in a first iteration. If the total number of candidate calc pixels found in the Tr image in the first iteration is too large (as a non-limiting example, more than 150) then the provisional threshold of 40 is raised, e.g., to 41, and the process is repeated to provisionally classify as candidate calc pixel those having pixel values greater than 41. If the initial iteration yields a total number of calc pixels that is too low (as a non-limiting example, less than 50) the initial threshold is lowered, e.g., to 39, and the process is repeated. These iterations are repeated until the total number of candidate calc pixels is in the desired range, for example and without limitation, in the range of 50 to 150 calc pixels for the given Tr image. The specific initial threshold, the size of the steps by which it is raised or lowered, and the desired range of total number of candidate calc pixels can be set depending on user preferences, either as part of the design process or as a parameter that can be set by service personnel or by the user of the system in the field, or on the basis of a study of typical values for a large population of breast images. This step yields a first provisional set of calc pixels.

2. Form a second provisional set of candidate pixels by excluding those associated with large areas in a Tr image that contain contiguous, i.e., connected, or nearly contiguous candidate calc pixels. As a non-limiting example, exclude from the first provisional set the candidate calc pixels associated with areas greater than 0.31 square mm (e.g. an area of about 30 pixels). The test can be for an area of only contiguous pixels provisionally identified as calc pixels, or it can be for areas in which any provisionally identified calc pixel is spaced by no more than one (or a set multiple of) pixels that are not calc pixels. This removes calcifications that would be clearly visible, or of little clinical relevance, in a Tr image so there is no need to point them out to the health professional and, moreover, if left in the displayed images they might obscure other, smaller calcification that should be pointed out.

3. Form a third provisional set of calc pixels by removing from the second provisional set the pixels that are generally arranged in lines that have excessive lengths. These linear groups of candidate calc pixels may be associated with blood vessels or other structures that may be of less interest than other calcifications. For example, a line of contiguous or nearly contiguous candidate calc pixels that is more than 2-4 mm long may be considered too long in this step. The term nearly contiguous is used in this patent specification to denote calc pixels that might be separated by one (or a set multiple of) non-calc pixels.

4. Form a fourth provisional set of calc pixels by removing from the third set the candidate calc pixels that do not have as contiguous neighbors, candidate calc pixels in at least two adjacent Tr images, as they are likely to be image noise.

5. Combine the thin-slice Tr images that still have candidate calc pixels into thick-slice Tr images to facilitate volume analysis. As a non-limiting example, add and if desired normalize, each set of three contiguous Tr images into a respective thick-slice Tr image by forming a new pixel by adding the values of three contiguous pixels in a direction transverse to the planes of the Tr images and dividing the result by three. As an alternative, combine into a thick-slice Tr image the several Tr images that contain candidate calc pixels forming in 3D a clump of candidate calc pixels, e.g., a 3D clump of candidate calc pixels that have at least a specified density (ratio of all pixels to candidate calc pixels, or the reverse).

6. Form a fifth set of candidate calc pixels by removing from the fourth set the candidate calc pixels that are arranged in lines that are too long in any direction (e.g. more than 2-4 mm) in a thick-slice Tr image and, therefore, are likely to be associated with structures such as ligaments, blood vessels, or cyst walls.

7. Form a sixth set of candidate calc pixels by eliminating from the fifth set the candidate calc pixels that are not in a set of at least a specified number of candidate calc pixels in a specified volume of the 3D set of pixels, e.g., in a volume that represents a 1 cm by 1 cm by 3 mm volume of the breast, where the 3 mm is the size of the thick slice Tr image.

8. Form a seventh set of candidate calc pixels by eliminating from the sixth set the candidate calc pixels that are too low in density in the 3D volume of pixels. For example, eliminate candidate calc pixels that are in a volume of the 3D set of pixels of a specified size in which there is too low a ratio of (a) total number of calc pixels in the volume to (b) the number of candidate calcs, where a candidate calc consists of connected calc pixels. As a non-limiting example, a ratio less than 1.1 in a volume of 1 cm by 1 cm by 3 mm can be considered too low. This step tends to eliminate candidate calcs that may represent image noise.

9. Form a final set of calc pixels by eliminating from the seventh set the candidate calc pixels that are in the first and last set of Tr images, as they are likely to correspond to pixels related to breast skin. As a non-limiting example, the candidate calc pixels from the first and last 1-3 Tr images in a stack of Tr images may be eliminated in this step.

10. Project the final set of calc pixels onto an image plane that is orthogonal to the planes of the Tr images to thereby form a scout image such as image 10 in FIG. 1. If desired, enhance the projected calc pixels so that they would stand out better in image 10. For example, increase the pixel values of the calc pixels in the final set to a higher value so that they appear as brighter spots in the scout image and/or increase the sizes of spots in the scout image that represent determined calcifications by setting to a higher or highest pixel value the pixels that are within a specified distance from a calc pixel that is in the final set.

11. Provide user interface and interaction between arrows in the scout images 10 and Tr images 12 for display as in FIG. 1, for example by including in display unit 122 appropriate user interface devices such as a mouse or other pointer to enable the user to click on selected arrows in image 10 and to make the system respond to the clicks as described above$_{[c1]}$.

12. Selectively enhance calcifications in images 12, by increasing their brightness and/or size, comparable to the enhancement of the scout image 10 described in step 11 above.

13. Provide for user interaction in selecting display of images 12 with or without such enhancement by higher brightness of pixels representing calcifications in images 12, for example by including in display unit 122 appropriate user interface devices such as a mouse or other pointer to enable the user to click on image 12 or some other display portion to toggle between a Tr image with or without enhanced calcifications and/or to toggle between the display of a thin-slice Tr image and the display of a thick-slice Tr image. For example, a thin-slice Tr image can represent a 1 mm thick slice of breast tissue while a thick-slice Tr image can represent a 3 mm or thicker slice of breast tissue$_{[c2]}$.

14. Provide for user interaction in selecting display of images 12 with or without such enhancement by higher brightness of pixels representing calcifications in images 12, by slabbing a given number of slices to form a thick slice. In slabbing, the calc pixels may be slabbed independently of the image pixels that are not identified as calc pixels. The term "slabbing" is used here in the sense of "combining" or "integrating" parameters of the pixels of images representing thinner slices into pixels of an image representing a thicker slice. Various known slabbing techniques can be used such as averaging with or without normality after, median, mode, maximum, MIP and/or other operations for collapsing columns of pixels.

15. Provide for user interaction in selecting display of images 12 with or without such enhancement by higher brightness of pixels representing calcifications in images 12, by slabbing calc pixels belonging to an identified cluster, where the slabbed calc pixels are shown on a specified slice. The image pixels that are not calc pixels, in those slices that contain calc pixels, may or may not be slabbed.

Figure 3:
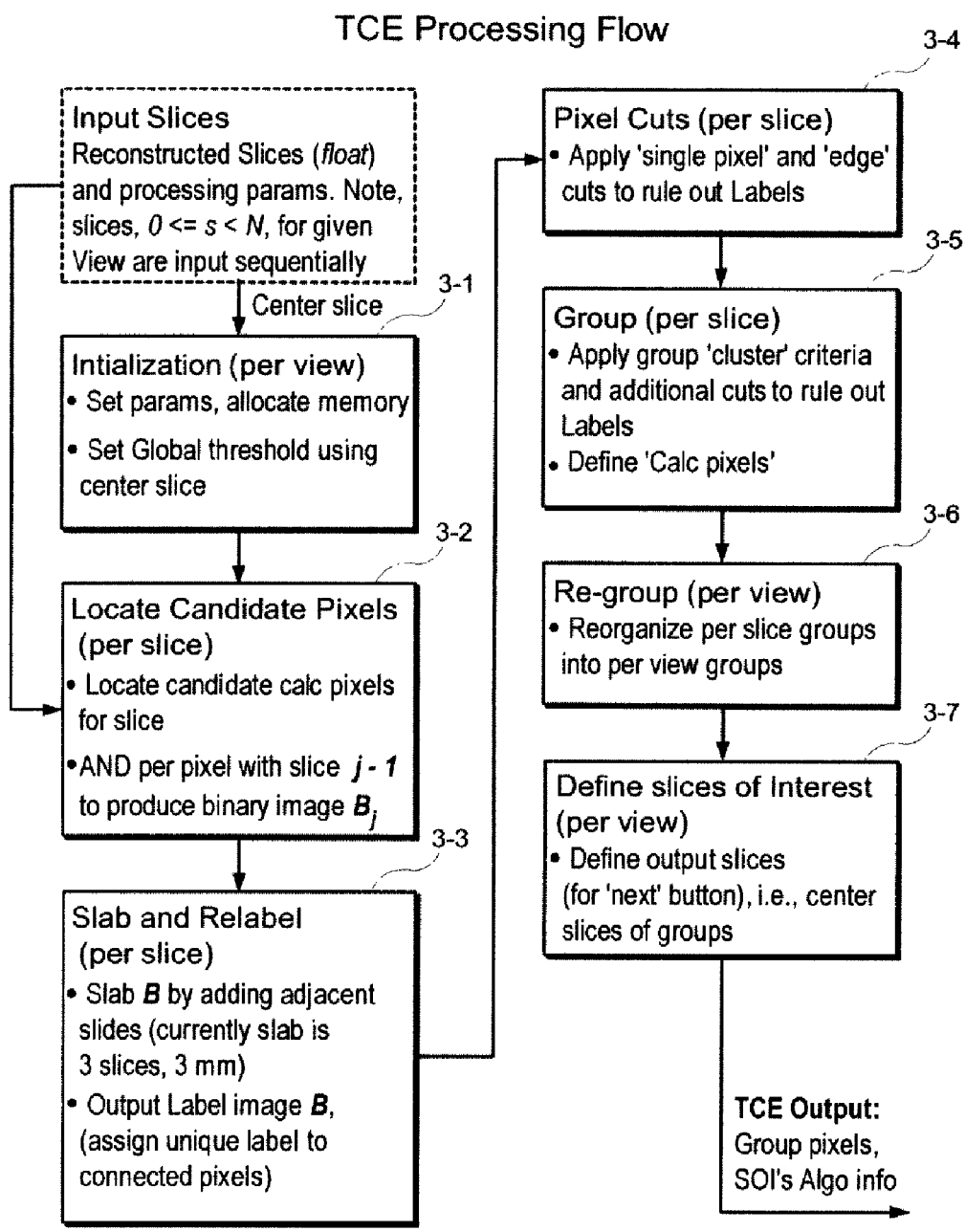
FIG. 3 is a flowchart illustrating an embodiment of a new process.

FIG. 3 illustrates a particular implementation of a process related to the above-described example. The process of FIG. 3 starts with inputting data describing the reconstructed images Tr for a given view, e.g., the Tr images reconstructed from the Tp images taken when the breast is imaged in a position suitable for a CC or an MLO view. The numbered steps discussed below correspond to the blocks of FIG. 3.

3-1. Initialization

The input Tr images are reconstructed images representing breast tissue slices, where the pixel values outside the breast area are constant (i.e., the image has been masked by previous processing). During initialization global parameters are defined, and adjusted for pixel size, and memory is allocated to process the given Mammographic View; which in this case is a Tr image. A global threshold is defined using a specified slice, for example, the center slice in the stack (View) as follows.

1. From input slice image $O_i$, where the subscript refers to the slice number, create smooth slice image, $S_i$ using a 5×5 boxcar filter)
2. Create Unsharp mask image $U_i=O_i-S_i$, where the typical range of values in $U_i$ is −60 to +60
3. Threshold images $U_i$ with fixed initial threshold of 40 to produce binary image $B_i$
   $B_i=0$ if $U_i<40$
   $B_i=1$ if $U_i>=40$
4. Label pixels in $B_i$ to produce Label image $L_i$ (the label image assigns a unique label to any connected positive value pixels in B)
5. Calculate label density as follows Labdense=(Nlab/bfrac)

bfrac=# of pixels in breast/total number of pixels
Nlab=number of labels
Check if Labdense is within a specified fixed range and adjust the threshold if needed as follows. If Labdense<LabdenseMin, lower the threshold by 1.0 If Labdense>=LabdenseMax, raise the threshold by 1.0
Where LabdenseMin=1000 and LabdenseMaz=2500
If Labdense is within the range, return initial threshold. If outside range, iterate steps 3-5, adjusting threshold, until within range. The maximum allowed iterations is 15.

The resultant threshold is used for all subsequent slices. Note that the method for calculating threshold can also be used for each slice separately.

3-2. Locate Candidate Pixels per Slice

Create Label image for each Tr slice image using steps 1-4 in Section 1. The first and last 3 Tr slice images, near the skin surfaces, are not included in the calculation to rule out skin-calcs.

Subject the label image to the following 'Cuts'.
1. Pixel Population Cut
   Delete labels that have more than Nmax pixels where
   Nmax=MaxPixArea/PixSize$^2$
   PixSize=size of pixels in mm
   MaxPixArea=0.3 mm$^2$ 2. Range Cut
   a. Calculate the linear extent of labels in x and y
   b. Delete labels that have an extent (in either direction) larger than 0.63 mm
3. Boundary Cut
   a. Delete labels that are close to the breast boundary. Currently, if a label pixel is within 3 mm of the skin edge, it is deleted.

Perform the logical AND of the new label image (after being subject to the previous cuts) and previous slice label image $L_{i-1}$ to produce binary image K.

$$K_i = L_i \,\&\&\, L_{i-1}$$

3-3. Slab and Re-label

The candidate image $K_i$ is 'slabbed' (as a non-limiting example, added on a per pixel basis) with adjacent slices to give binary Slab image $S_i$. The slabbing is per pixel and uses 3 contiguous slices.

$$S_i = 1 \text{ if } \text{SUM}(K_{i-1}, K_i, K_{i+1}) > 0$$
$$= 0 \text{ otherwise}$$

A running sum may be used for efficiency if the Tr slice images are input consecutively. In the running sum method, the first slice of the previous slab is subtracted and the current slice is added to the slab image. $S_i$ is then Re-labeled to give new label image $M_i$.

3-4. Pre Group Pixel Cuts

Apply additional Cuts to Label image M computed in step 3

4.1 Single Pixel Cut

Delete single pixel candidates with very low attenuation, i.e., on the visual threshold, or possible noise. Let the image pixel value of M be $V_j$ where j is the image pixel index (0<j<Nxy), and Nxy is the total number of pixels per slice. For each identified calc pixel j, calculate $N_g$ as follows $$N_g = \Sigma_k (f \times \{1, \text{if } V_j > V_{j+k}\, 0, \text{if } V_j \leq V_{j+k}\}$$

where k={−2,2,2*Nx,−2*Nx,1−Nx,−1−Nx,1+Nx,Nx−1}
f=1.04
Nx=number of columns in the image.
if $N_g<8$, unset Label pixel j in M.

4.2 Edge Cut

Remove label pixels that are located on edges, e.g., ligaments, artifact edges, breast skin folds.
1. Search for peaks in pixel intensity along x direction starting with candidate labeled pixel as center. The search distance is ±0.8 mm from the center labeled pixel. Extract a line L of pixel values along the x-dimension with the center point being a calc pixel. The length of L is 1 mm.
2. Calculate the peak (maximum value) and maximum derivative value, $L_i - L_{i-1}$, of L.
3. If peak is above a threshold (=30), count as valid peak.
4. Repeat steps 2-4 for pixel centers located at ±N (perpendicular to line L) from the calc pixel, where N=0.8 mm/(pixel size). Sum the number of valid peaks and calculate the average maximum derivative.
5. If number of valid peaks is above the maximum (=1.6 mm/(pixel size)−1) unset the calc Label pixel in M
6. If average maximum derivative is above a threshold (=150), unset calc Label pixel in M.
7. Repeat steps 1-7 searching along the y direction instead of x. The lines L being along the y-direction.
8. Repeat steps 1-8 for all labeled pixels.

3-5. Per Slice Grouping

Apply group (cluster) criteria.
For each Valid label in $M_j$ that passed all previous cuts:
1. Search neighborhood (±5 mm) and sum all Labels. If sum is greater than 2, assign a group label, otherwise unset Label. This keeps all clusters of 3 calcs within a 1 mm square.

5.1 Post-Group Cuts

After group Labels have been assigned, apply additional cuts to each group.
1. Calculate Calc Pixel Density, CPD CPD=(Number of pixels in group)÷(Number of labels (calcs) in group)

2. If CPD≧$CPD_{min}$(=3), do not apply any additional cuts, and do not delete the group.
3. If CPD<$CPD_{min}$ apply the following cuts in order.
3.1 If CPD<1.1, delete group. Otherwise proceed with Cut 3.2
3.2 Calculate $\Delta_{nn}$ $$\Delta_{nn} = \text{Ave}(C) - \text{Ave}(N)$$

Ave(C)=average pixel value of labels in the group.
Ave(N)=average pixel value of neighboring pixels (nearest neighbors of C)
In the average calculations only labels that have less than 3 pixels are considered. If the number of labels used in the average is greater than 0.6×(total number of labels in group), apply the following cuts.
If ($\Delta_{nn}<25$) delete group
If ($\Delta_{nn}<42 \,\&\&\, \text{CPD}<1.7$) delete group
If group not deleted proceed with Cut 3.3.
3.3 Fit a $3^{rd}$ order polynomial to the distribution of labels within the group. If the x-extent of the group is greater than the y-extent, x is the dependent variable, otherwise y is the dependent variable. Calculate the normalized chi-squared of the fit, Nchi=chi-squared÷Number of points used in fit If Nchi<0.10 delete group 3-6. Volume Grouping Regroup the valid labels in the volume (slice stack) such that labeled pixels that are within ±10 mm in x,y, and ±5 mm in z, are in the same group. This connects groups that may exist over several slices and may contain a slice with no labeled pixels. This step combines the previous per slice groups that may overlap (or be close) in the volume.

3-7. Slices of Interest

Calculate the SOI's 'slices of interest' for the view. SOI's are those slices which may be used in the Viewing application that will allow the user to quickly scroll the TCE identified slices within a View.

A SOI is defined for each identified group as the slice that contains the most labeled pixels in that group. Note that 2 different groups may have the same SOI.

Some other possible methods include:
1. Finding calcifications using the Tp data, and identifying the calcification locations on the Tr dataset for display, as described.
2. Finding calcifications using both the Tp and the Tr data, and identifying the calcification locations on the Tr dataset for display as described. Using both Tp and Tr may improve the accuracy or computational efficiency of the calc determination algorithm[c3]. Methods for identifying calcifications in Tp are known, such as shown in the material incorporated by reference herein. Once potential calcifications in Tp are found, their possible locations in Tr can be determined through reconstruction of the locations found in the Tp images, such as described in the material incorporated by reference herein.

3. A similar method can be used to identify possible pathology masses, and lesions containing both masses and calcs. Methods of identifying possible pathology masses are given in the material, herein incorporated by reference. An inventive feature here is the user interface whereby only slices are shown that have either masses or calcs or both. The CAD algorithm can use either Tr or Tp or both datasets to do its determination.

4. In the above-described approach, the display of a given slice might contain calcifications (or masses) from other slices, especially if they have been ascertained to be part of the same cluster. If desired, a different highlighting can be applied to calcs or masses that also are present in adjacent Tr slices that are not displayed at the moment.

5. Instead of displaying only breast slice images that include pixels determined to be calcifications, display all breast slice images or at least a subset of all breast slice images, including some that do not have such pixels, such that the user can scroll through those images. The user can be helped to identify the calc pixels, particularly if their brightness is enhanced as discussed above, by the sudden change in brightness in scrolling from one displayed slice image to the next or help can be provided by marking the calc, e.g. with some symbol. Then change from one slice image to another can be directed manually by the user, or the display can be automated to present the succession of slice images in cine format.

6. Instead of or in addition to identifying talcs, the process can be adapted to identify masses using for example CAD techniques such as those described in the material incorporated in this patent specification by reference. Suspected abnormalities can then be selectively specified to be (1) only calcifications, (2) only masses, and (3) both calcifications and masses. The selection and display of masses can then be similar to the selection and display of calcifications described above.

7. Instead of the process described above to identify abnormalities corresponding to suspected calcifications, a simpler process can be used such as a filter that identifies all pixels in a Tp and/or Tr image that meet specified threshold criteria of pixel values selected to identify pixels likely to correspond to calcifications. Known techniques can be used to eliminate from an initial cut those abnormalities that are likely to represent noise, such as isolated single pixels that meet the threshold criteria or very small groups of such pixels. The remaining suspected abnormalities can then be displayed as described above.

An alternative or additional process involves finding likely calcification in the individual 2D Tp and/or Mp images and then searching only subsets of the 3D Tr images to select corresponding Tr images for selective display to the user. This can be implemented by initially searching Tp and/or Mp images rather than the 3D set of Tr images to identify likely calcifications of interest. The initial search of 2D images can be done using CAD as disclosed in the patent literature incorporated by reference in this patent specification, or by adapting the principles discussed above for identifying calcifications in Tr images and 3D volumes, or in some other manner. After likely calcifications of clinical significance are identified in the 2D Tp and/or Mp images, the 2D images can be displayed one at a time or several at a time, or only those 2D images that have identified calcifications can be displayed. When a user points to a likely calcification in a displayed 2D image, e.g., by a mouse click on the calcification in a 2D image, computer processing can search through the Tr images of the breast to identify and display the Tr image or Tr images that contain that calcification. This search through the Tr images can use knowledge about the location of the likely calcification in the 2D image, on parameters of the calcification such as its size, shape, pixel values and distribution of those values in the 2D image, and possibly other parameters. In case of an ambiguity, i.e., the calcification pointed to in the 2D image appears in two or more Tr images, all possibly relevant Tr images can be displayed to the user, singly or in a set or subsets or in cine mode, and the user may select for further use the ones that appear relevant or dismiss any that are not. This alternative can reduce processing time because the search for likely calcifications in the 2D images can be faster, and the subsequent search for the Tr slice(s) that contain a calcification to which the user pointed in a 2D image also can be faster. One reason for greater computational efficiency is that the 3D data set (the Tr images) need to be processed only after a likely calcification has been selected, so only a relatively small volume of the 3D set would need to be searched. Another advantage of this alternative may be if the search process is more sensitive and/or more accurate for 2D images. If so, then it is more likely to decrease the overall rate of false negatives and/or false positives in identifying likely calcifications, and thus improve the presentation of images to the health professional and make the overall process of assessing the images for screening, diagnosis, or other purposes, more effective anti/or more efficient.

As another alternative or additional process, the user can point to any feature in one of the 2D images, not necessarily a likely calcification, even in 2D images that have not been processed to identify likely calcifications, and the process can attempt to identify and display for the user the Tr slice(s) in which that feature can be seen well, e.g., the feature is in best focus. The search through the 3D set of pixel data can use information about the feature to which the user pointed, such as location in the 2D image, size, shape, pixel values and distribution of those values, and possibly other parameters. If the feature is relatively unique and small, the process may correctly identify and display for the user one or only a few Tr slices. In other cases, such as in the case of a relatively large mass, or in the case of a feature in the 2D image that represents a superposition of two or more features in the breast that are along the x-ray beam path to that feature in the 2D image, there may be ambiguities as to which Tr image or images show the feature to which the user has pointed. Again, in such a case the process may similarly display the possibly pertinent Tr slices, or may display only those that meet a threshold of relevance, e.g., based on a calculation of their degree of relevance to the feature to which the user pointed.

The examples described above are only illustrative and other examples also are encompassed within the scope of the appended claims. The parameters given as example above, such as initial thresholds, sizes of areas or volumes, etc. can be modified by those skilled in the art without departing from the invention described in the appended claims. Other variations can be introduced without departing from the spirit of the disclosure or from the scope of the appended claims. For example, elements and/or features of different illustrative embodiments may be combined with each other and/or substituted for each other, and the steps of the example described in detail above can be rearranged and steps can be omitted or added within the scope of this disclosure and appended claims.

The invention claimed is:

1. A method of acquiring and displaying x-ray images comprising:
   acquiring x-ray tomosynthesis image data Tp representative of projection images Tp taken at different angles of an origin of imaging x-rays relative to a patient's breast;
   computer-processing at least a subset of the acquired Tp data into reconstructed tomosynthesis image data Tr representative of images Tr of slices of the breasts that have selected orientations and thicknesses;
   identifying one or more suspected abnormalities that meet selected criteria of size, location and other properties by computer-processing said Tr data; and
   selectively displaying a representation of the identified suspected abnormalities in association with displaying selected images related to said Tr data.

2. A method as in claim 1 in which the step of selectively displaying comprises displaying indications of the identified suspected abnormalities arranged in a direction that is not parallel to a plane of a concurrently displayed Tr image.

3. A method as in claim 1 in which said step of selectively displaying comprises displaying a representation of suspected abnormalities as a scout view projection of said suspected abnormalities on an image plane that is angled relative to that of a concurrently displayed Tr image.

4. A method as in claim 3 including at least an indication of level in the scout view of a location of a concurrently displayed Tr image.

5. A method as in claim 1 including displaying one or more marks around or adjacent respective identified suspected abnormalities in a displayed Tr image.

6. A method as in claim 1 including selectively enhancing brightness of suspected abnormalities visible in a displayed Tr image.

7. A method as in claim 1 in which said suspected abnormalities are suspected calcifications.

8. A method of acquiring and displaying x-ray images comprising:
   acquiring x-ray tomosynthesis image data Tp representative of projection images Tp taken at different angles of an origin of imaging x-rays relative to a patient's breast;
   computer-processing at least a subset of the acquired Tp data into reconstructed tomosynthesis image data Tr representative of images Tr of slices of the breasts that have selected orientations and thicknesses;
   identifying one or more suspected abnormalities that meet selected criteria of size, location and other properties by computer-processing said Tp and/or Tr data; and
   selectively displaying a representation of the identified calcification in association with displaying selected images related to said Tr data.

9. A method as in claim 8 in which said identifying comprises processing at least a subset of each of said Tp and of said Tr data.

10. A method as in claim 8 in which said suspected abnormalities are suspected calcifications.

11. A method of acquiring and displaying x-ray images comprising:
    acquiring x-ray tomosynthesis image data Tp representative of projection images Tp taken at different angles of an origin of imaging x-rays relative to a patient's breast;
    computer-processing at least a subset of the acquired Tp data into reconstructed tomosynthesis image data Tr representative of images Tr of slices of the breasts that have selected orientations and thicknesses;
    identifying one or more suspected abnormalities that meet selected criteria of one or more of number, size, location and other properties by computer-processing said Tr and/or Tp data; and
    selectively displaying only images of those slices of the breast that contain suspected abnormalities identified in said identifying step.

12. A method as in claim 11 in which said suspected abnormalities are suspected calcifications.

13. A method of acquiring and displaying x-ray images comprising:
    acquiring x-ray tomosynthesis image data Tp representative of projection images taken at different angles of an origin of imaging x-rays relative to a patient's breast;
    computer-processing at least a subset of the acquired Tp data into reconstructed tomosynthesis image data Tr representative of images Tr of slices of the breasts that have selected orientations and thicknesses;
    identifying suspected abnormalities that correspond to suspected calcifications and suspected masses in the breast that meet selected criteria of number, size, location and other properties by computer-processing said Tr and/or Tp data; and
    selectively displaying images of breast slices with visible indications therein of (1) identified abnormalities that are in a currently displayed image of a slice, and (2) identified abnormalities a are in another image of a slice.

14. A method of acquiring and displaying x-ray images comprising:
    acquiring x-ray tomosynthesis image data Tp representative of projection images taken at different angles of an origin of imaging x-rays relative to a patient's breast;
    computer-processing at least a subset of the acquired Tp data into reconstructed tomosynthesis image data Tr representative of images Tr of slices of the breasts that have selected orientations and thicknesses;
    identifying one or more breast image portions that correspond to suspected calcifications and/or masses in the breast that meet selected criteria of number, size, location and other properties by computer-processing said Tr and/or Tp data through a process that also identifies geometric relationships between identified abnormalities found in different slice images; and
    selectively displaying images of breast slices with visible indications therein of suspected abnormalities that span more than one breast slice.

15. A method of acquiring and displaying tomosynthesis images comprising:
    acquiring projection x-ray images of a patient's breast at different angles and reconstruction initial breast slice images in a reconstruction process using at least the projection images;
    identifying pixels that are in respective initial slice images and correspond to suspected abnormalities at least in part by computer-processing at least some of said images;
    combining initial slice images into final slice images using a computer-implemented slabbing process that combines pixels that correspond to suspected abnormalities in a different manner from pixels that do not; and
    displaying the final slab images in a manner that enhances slabbed pixels that correspond to suspected abnormalities.

16. A method as in claim 15 in which the slabbing process comprises combining values of pixels that are in geometrically corresponding locations in a selected number of two or more initial slice images.

17. A method as in claim 16 in which said slabbing process comprises adding the values of both pixels that correspond to suspected abnormalities and pixels that do not.

18. A method as in claim 16 in which said slabbing process comprises adding the values of pixels that correspond to suspected abnormalities but not of pixels that do not.

19. A method as in claim 15 in which the suspected abnormalities comprise calcifications.

20. A method of acquiring and displaying tomosynthesis images comprising:
acquiring projection x-ray images of a patient's breast at different angles and reconstruction breast slice images in a reconstruction process using at least the projection images;
identifying pixels in the projection and/or reconstructed images that correspond to suspected abnormalities in breast tissue at least in part by computer-processing at least some of said images; and
computer-processing the identified pixels to facilitate visualization of at least a subset of the identified pixels in a display; and
displaying at least selected slice images containing said subset of the identified pixels for screening and/or diagnosis by a user.

21. A method as in claim 20 in which said identifying comprises identifying pixels that are likely to correspond to suspected abnormalities in the breast that meet selected criteria pertaining to at least one of calcifications and masses in the breast.

22. A method as in claim 21 in which the identifying step comprises relaxing or making stricter said criteria to control a relationship between the number of identified suspected abnormalities and selected limits.

23. A method as in claim 22 in which said displaying comprises selectively displaying (1) only slice images that contains suspected abnormalities, or (2) both slice images that contain suspected abnormalities and slice images that do not.

24. A method as in claim 23 in which said displaying comprises displaying slice images in a cine sequence.

25. A method as in claim 20 in which said identifying comprises identifying pixels that are likely to correspond to masses in the breast that meet selected criteria.

26. A method as in claim 20 in which said processing comprises slabbing a plurality of slice images by combining geometrically related pixels of different slice images in a manner that differs between combining pixels identified as corresponding to suspected abnormalities and combining pixels that have not been so identified.

27. A method as in claim 20 in which said processing comprises slabbing a plurality of slice images into a single image for display, where the slabbing forms said single image from slice images that contain a cluster of pixels identified as corresponding to suspected abnormalities.

28. A method as in claim 20 in which the suspected abnormalities comprise calcifications.

29. A system for acquiring and displaying tomosynthesis images comprising:
an x-ray acquisition unit acquiring projection x-ray images of a patient's breast at different angles;
a processing and image reconstruction unit coupled with said acquisition unit and configured to receive said projection images therefrom and reconstruct breast slice images in a reconstruction process using at least said projection images;
said processing and image reconstruction unit being further configured to identify pixels in the projection and/or reconstructed slices images that correspond to suspected abnormalities in breast tissue and to process the identified pixels to facilitate visualization of at least a subset of the identified pixels in a display; and
an image display unit displaying at least selected slice images containing said subset of the identified pixels for screening and/or diagnosis by a user.

30. A system as in claim 29 in which the suspected abnormalities comprise calcifications.

31. A computer program product embodied in an information storage device and containing instructions to a processing system to:
receive information describing projection x-ray images of a patient's breast acquired at different angles and reconstruct breast slice images in a reconstruction process using at least the projection images;
identify pixels in the projection and/or reconstructed images that correspond to suspected abnormalities in breast tissue;
process the identified pixels to facilitate visualization of at least a subset of the identified pixels in a display, and
deliver information describing for display at least selected slice images containing at least said subset of the identified pixels for screening and/or diagnosis by a user.

32. A computer program product as in claim 31 in which the suspected abnormalities comprise calcifications.

33. A method of acquiring and displaying x-ray images comprising:
acquiring x-ray tomosynthesis image data Tp representative of projection images taken at different angles of an origin of imaging x-rays relative to a patient's breast;
computer-processing at least a subset of the acquired Tp data into reconstructed tomosynthesis image data Tr representative of images Tr of slices of the breasts that have selected orientations and thicknesses;
selectively displaying a subset of Tr data that contain selected features of interest in tissue of said breast present in said image data Tp and/or Tr.

34. A method as in claim 33 in which the suspected abnormalities comprise calcifications.

35. A method of acquiring and displaying x-ray images comprising:
acquiring x-ray tomosynthesis image data Tp representative of projection images Tp taken at different angles of an origin of imaging x-rays relative to a patient's breast;
computer-processing at least a subset of the acquired Tp data into reconstructed tomosynthesis image data Tr representative of images Tr of slices of the breasts that have selected orientations and thicknesses;
identifying one or more suspected abnormalities in said images Tp and/or Tr that meet selected criteria of at least a subset of number, size, location and other properties of pixels by computer-processing said Tr data; and
selectively displaying a representation of the identified suspected abnormalities in association with displaying selected images related to said Tr data.

36. A method as in claim 35 in which the step of selectively displaying comprises displaying indications of the identified suspected abnormalities arranged in a direction that is not parallel to a plane of a concurrently displayed Tr image.

37. A method as in claim 36 in which said step of selectively displaying comprises displaying a representation of suspected abnormalities as a scout view projection of said suspected abnormalities on an image plane that is angled relative to that of a concurrently displayed Tr image.

38. A method as in claim 35 including identifying slices that contain any of said suspected abnormalities, wherein the step of selectively displaying comprises selectively displaying only images of the identified slices of the breast.

39. A method of acquiring and displaying x-ray images comprising:
   acquiring x-ray tomosynthesis image data Tp representative of projection images taken at different angles of an origin of imaging x-rays relative to a patient's breast;
   computer-processing at least a subset of the acquired Tp data into reconstructed tomosynthesis image data Tr representative of images Tr of slices of the breasts that have selected orientations and thicknesses;
   identifying one or more portions of the breast abnormalities that correspond to suspected abnormalities in the breast that meet selected criteria of one or more of number, size, location and other properties by computer-processing said Tr and/or Tp data; and
   selectively displaying images of breast slices with visible indications therein of (1) identified suspected abnormalities that are in a currently displayed image of a slice, and (2) identified suspected abnormalities that are in another image of a slice.

40. A method as in claim 39 in which the suspected abnormalities comprise calcifications.

41. A method of acquiring and displaying x-ray images comprising:
   acquiring x-ray tomosynthesis image data Tp representative of projection images taken at different angles of an origin of imaging x-rays relative to a patient's breast;
   computer-processing at least a subset of the acquired Tp data into reconstructed tomosynthesis image data Tr representative of images Tr of slices of the breasts that have selected orientations and thicknesses;
   identifying one or more portions of the breast that correspond to suspected abnormalities in the breast that meet selected criteria of one or more of number, size, location and other properties by computer-processing said Tr and/or Tp data through a process that also identifies geometric relationships between identified abnormalities found in different slice images; and
   selectively displaying images of breast slices with visible indications therein of clusters of abnormalities that span more than one breast slice.

42. A method as in claim 41 in which the suspected abnormalities comprise calcifications.

43. A method of acquiring and displaying x-ray images comprising:
   acquiring two-dimensional (2D) x-ray image data of a patient's breast, including tomosynthesis image data Tp representative of projection images Tp taken at different angles of an origin of imaging x-rays relative to the breast;
   computer-processing at least a subset of the acquired 2D x-ray image data into reconstructed tomosynthesis image data Tr representative of images Tr of slices of the breasts that have selected orientations and thicknesses;
   identifying suspected abnormalities that meet selected criteria of one or more of number, size, location and other properties at least in part by computer-processing at least a subset of said 2D image data; and
   automatically identifying and displaying under user control Tr images showing the suspected abnormalities identified in said Tp images.

44. A method as in claim 43 including selectively displaying 2D images based on said 2D image data with identified suspected abnormalities therein, and wherein said user control comprises a user pointing with a computer interface device to one or more suspected abnormalities in the displayed 2D images.

45. A method as in claim 43 in which the suspected abnormalities comprise calcifications.

46. A method of acquiring and displaying x-ray images comprising:
   acquiring two-dimensional (2D) x-ray image data of a patient's breast, including tomosynthesis images data Tp representative of projection images Tp taken at different angles of an origin of imaging x-rays relative to the breast;
   computer-processing at least a subset of the acquired 2D x-ray image data into reconstructed tomosynthesis image data Tr representative of images Tr of slices of the breasts that have selected orientations and thicknesses;
   selectively displaying one or more 2D images based on at least of subset of said 2D image data and identifying, at least in part through computer processing of at least some of said 2D images, one or more features in the displayed 2D images in response to user designation of said features; and
   automatically identifying and displaying under user control Tr images showing the one or more features identified in said displayed 2D images.

47. A method as in claim 46 in which the suspected abnormalities comprise calcifications.

* * * * *